United States Patent [19]

Chamberlin, Sr.

[11] Plant 5,139

[45] Nov. 15, 1983

[54] PEACH TREE

[75] Inventor: Thomas O. Chamberlin, Sr., Visalia, Calif.

[73] Assignee: H. P. Metzler & Sons, Inc., Del Rey, Calif.

[21] Appl. No.: 324,257

[22] Filed: Nov. 23, 1981

[51] Int. Cl.[3] ..... A01H 5/00

[52] U.S. Cl. ..... Plt./43

[58] Field of Search ..... Plt./43

*Primary Examiner*—James R. Feyer

*Attorney, Agent, or Firm*—Huebner & Worrel

[57] ABSTRACT

A peach tree, denominated "July Sun", of very vigorous growth producing very large freestone fruit having a bright red to a bright yellow coloration ripening after the July Lady Peach Tree about the twentieth of July.

1 Drawing Figure

BACKGROUND OF THE VARIETY

The present invention relates to a new and distinct variety of peach tree, denominated "July Sun", broadly characterized by its very vigorous growth producing very large freestone fruit and more particularly to such a peach tree wherein the fruit is of a bright red to bright yellow color having firm flesh of a bright yellow color with a very slight rim of red around the pit cavity and very good flavor and aroma and ripening about the twentieth of July in the San Joaquin Valley of California.

There is generally a direct relationship between the size of tree fruit and its commercial value. However, it is frequently the case that there is an inverse relationship between the size of the tree fruit and the quantity of the fruit grown. This is true in the case of peach trees as it is in the case of other tree fruit. In addition, tree fruit of larger size is often more difficult to handle and ship because of a susceptibility to bruising of the fruit as a result of delicate skin and flesh. Still further, there is a general tendency for varieties of peach trees which produce larger size fruit to produce fruit which is less brightly colored than varieties of smaller size. The fruit of the present invention is distinct in that it is of consistently large size even when the crop is large, it has very firm flesh and tough skin affording excellent handling and shipping characteristics, in brightly colored and has very good flavor and aroma.

ORIGIN AND ASEXUAL REPRODUCTION OF THE NEW VARIETY

The instant new variety of peach tree was discovered by myself in 1976 and is a newly found seedling of the July Lady peach tree. Seeds of the July Lady were planted in a plot in the nursery of H. P. Metzler & Sons, Inc. at 5286 South Del Rey Avenue, Del Rey, Calif. 93616 in 1974. The first fruit of the present variety was observed in 1976 and its distinctive characteristics discovered at that time. The present variety was asexually propagated under my direction at H. P. Metzler & Sons, Inc. in 1976 by grafting several seedlings with scions from the newly discovered seedling and then moving them to a test nursery on Ranch No. 18 of H. P. Metzler & Sons, Inc. at Del Rey, Calif. Subsequently, more seedlings were budded from the new variety and planted in the test plot. The seedlings of the new variety were observed in the nursery over several growing seasons and the fruit and tree characteristics resulting from such asexual reproduction proved to be identical to those of the original seedling of the new variety.

SUMMARY OF THE NEW VARIETY

The instant variety of peach tree is characterized by its quite vigorous growth consistently producing freestone fruit of very large size having a bright red to bright yellow color, very firm flesh of a bright yellow color having very good flavor and aroma, a tight pit cavity bounded by a very slight rim of red and a tough skin which with its very firm flesh facilitates handling and shipping.

BRIEF DESCRIPTION OF THE DRAWING

The accompanying drawing is a color photograph of five mature fruit of the instant variety, one positioned to show the stem, a second positioned to show the apex, a third positioned to show the side, a fourth sliced along the suture plane and the pit removed to expose the pit cavity and a fifth sliced along the suture plane with the pit left in place. A representative twig is also shown in the photograph with characteristic leaves.

DETAILED DESCRIPTION

Referring more specifically to the pomological details of this new and distinct variety of peach tree, the following characteristics were observed under the ecological conditions prevailing at the nursery of H. P. Metzler & Sons, Inc. at Del Rey, Fresno County, Calif. and is an outlined description thereof. All major color code plate identifications are by reference to the Color Name Chart of the Inter-Society Color Council, National Bureau of Standards.

TREE

Size: Large size and very vigorous growth with a normal form subject to variation by pruning methods.

Productivity: Very good.

Regularity of Bearing: Regular.

Trunk: Normal size with rough surface and normal color (62-d.g.y. Br.).

Branches: Normal size with rough surface of the same character as the trunk, normal color (62-d.g.y. Br.) and small size lenticels 8–10 per square inch.

Leaves: Normal size.

*Length.*—Average length from 6 inches [15.24 CM] to 7 inches [17.78 CM].

*Width.*—$1\frac{1}{4}$ inches [3.175 CM].

*Texture.*—Smooth and almost waxy.
*Shape.*—Lanceolate with apex acuminate.
*Margin.*—Crenate.
*Petiole.*—About ½ inch [1.27 CM] in length and 1/16 inch [0.15875 CM] thick.
*Glands.*—Reniform and of small size, with two opposed at base of leaf; color, yellow green (146 d.g.).
*Color.*—Normal. Upper side (147 v.d.g.) and under side (146 d.g.).

Flower buds: Small, round and slightly elongated with stamen extending from bud about 3/16 inch [0.47625 CM] while bud still closed.
*Diameter.*—¼ inch [0.635 CM].
*Length.*—7/16 inch [1.11125 CM].

Flowers:
*Date of bloom.*—March 7th.
*Size.*—Medium, each petal ½ inch [1.27 CM] in length when open and 5/16 inch [0.79375 CM] in width.
*Color.*—Outer edge of petal (2.S pink) and center of flower (4.1 pink).

FRUIT

Maturity: Reached in the San Joaquin Valley of California about July 20th or after July Lady peach tree.

Size:
*Very large.*—With many of 3½ inches [8.89 CM] to 4 inches [10.16 CM] in length. Diameter 2¾ inches [6.985 CM] to 4 inches [10.16 CM]. Transverse dimension in suture plane 3 inches [7.62 CM] or slightly more. Transverse dimension at right angles to suture plane 2¾ inches [6.985 CM] to 4 inches [10.16 CM].

Form: Uniform and symmetrical.
*Suture.*—Very smooth extending from the base to the apex 4 inches [10.16 CM].
*Ventril surface.*—Rounded to slightly flat.
*Stem cavity.*—Rounded and ½ inch [1.27 CM] in depth, ¾ inch [1.905 CM] in width.
*Apex.*—Slightly flat to round.
*Base.*—Wide and flat.
*Pistil point.*—Almost receding.

Stem:
*Size.*—Length 5/16 inch [0.79375 CM] and Caliper ⅛ inch [0.3175 CM].

Skin:
*Thickness.*—Medium.
*Texture.*—Strong, tough and tenacious to flesh.
*Tendency to crack.*—None.
*Pubescence.*—Medium.

*Color.*—Dark red (17 V deep red) to bright red (13 deep red) to strong yellow (83 Brill y).

Flesh:
*Color.*—Bright yellow (82 V yellow).
*Surface of pit cavity.*—Rough.
*Color of pit cavity.*—Red (11 V red).
*Juice.*—Very slightly acid taste.
*Texture.*—Smooth and very firm.
*Fibers.*—None.
*Ripening.*—Even.
*Flavor.*—Very good.
*Aroma.*—Good.
*Eating quality.*—Has crisp nature with very good flavor.

Stone:
*Type.*—Freestone.
*Fibers.*—None.
*Size.*—1⅜ inches [3.4925 CM] in length and 1⅛ inches [2.8575 CM] in width. Thickness, ¾ inch [1.905 CM].
*Shape.*—Ovoid. Straight base, pointed apex. Sides equal with heavy ridges that run generally from apex to base and are about ⅛ inch [0.3175 CM] in height.
*Color.*—Brown (43 m.r. Br.).
*Splitting tendency.*—None.

Use: Fresh market.
*Keeping quality.*—Good. Fruit has been kept in storage as long as four weeks without noticeable deterioration.
*Shipping quality.*—Due to firm nature of flesh and tough skin, fruit ships very well.

Although the new variety of peach tree possesses the described characteristics as a result of the growing conditions in Fresno County, Calif., in the Central portion of the San Joaquin Valley, it is to be understood that variations of the usual magnitude and characteristics incident to growing conditions, fertilization, pruning, pest control and other horticultural practices are to be expected.

Having thus described and illustrated my new variety of peach tree, what is claimed as new and desired to be secured by Letters Patent is:

1. A new and distinct variety of peach tree substantially as illustrated and described and which is characterized by quite vigorous growth producing freestone fruit of very large size, having a bright red to a bright yellow color, a tough skin, very firm flesh of bright yellow color having very good flavor and aroma and a pit cavity bounded by a very slight rim of red; and ripening about the twentieth of July.

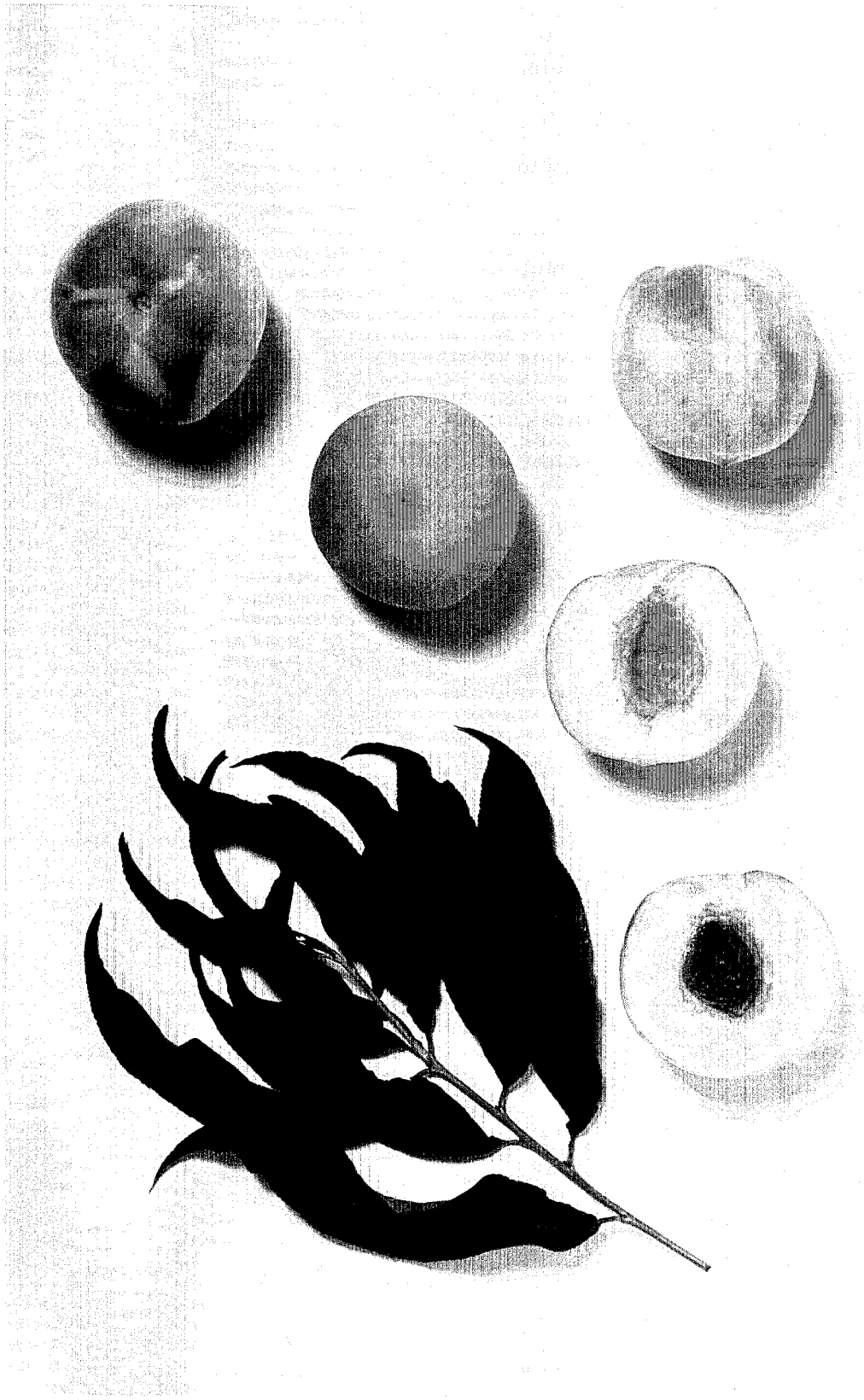

* * * * *